(12) United States Patent
He et al.

(10) Patent No.: US 10,941,356 B2
(45) Date of Patent: Mar. 9, 2021

(54) PARAXYLENE PRODUCTION FROM NAPHTHA FEED

(71) Applicant: Saudi Arabian Oil Company, Dhahran (SA)

(72) Inventors: Yufeng He, Al Khobar (SA); Qi Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/454,839

(22) Filed: Jun. 27, 2019

(65) Prior Publication Data

US 2020/0407651 A1    Dec. 31, 2020

(51) Int. Cl.
| | | |
|---|---|---|
| *C10G 59/00* | (2006.01) | |
| *C10G 59/02* | (2006.01) | |
| *C10G 61/08* | (2006.01) | |
| *C10G 7/00* | (2006.01) | |
| *C07C 15/08* | (2006.01) | |

(52) U.S. Cl.
CPC ............... *C10G 59/02* (2013.01); *C10G 7/00* (2013.01); *C10G 61/08* (2013.01); *C07C 15/08* (2013.01); *C10G 2400/30* (2013.01)

(58) Field of Classification Search
CPC ........ C10G 59/00; C10G 59/02; C10G 59/06; C10G 61/00; C10G 61/02; C10G 61/08; C10G 35/00; C10G 2400/30; C07C 15/08
See application file for complete search history.

(56) References Cited

U.S. PATENT DOCUMENTS

| | | | |
|---|---|---|---|
| 3,753,891 A | * | 8/1973 | Heinemann ............ B01J 29/40 208/62 |
| 4,310,715 A | | 1/1982 | Dorawala et al. |
| 4,341,914 A | | 7/1982 | Berger |
| 4,839,024 A | | 6/1989 | Ramage et al. |
| 5,847,256 A | | 12/1998 | Ichioka et al. |
| 5,866,741 A | | 2/1999 | Wu et al. |
| 6,004,452 A | | 12/1999 | Ash et al. |
| 6,051,128 A | | 4/2000 | Nacamuli et al. |
| 6,096,938 A | | 8/2000 | Ghosh |
| 6,602,404 B2 | | 8/2003 | Walsh et al. |
| 8,882,994 B2 | | 11/2014 | Moser et al. |
| 8,926,828 B2 | | 1/2015 | Serban et al. |
| 9,000,247 B2 | | 4/2015 | Abudawoud |
| 9,206,362 B2 | | 12/2015 | Haizmann et al. |

(Continued)

OTHER PUBLICATIONS

PCT International Search Report and Written Opinion issued in International Application No. PCT/US2020/039596 dated Sep. 10, 2020, 15 pages.

*Primary Examiner* — Prem C Singh
*Assistant Examiner* — Brandi M Doyle
(74) *Attorney, Agent, or Firm* — Fish & Richardson P.C.

(57) ABSTRACT

Increased paraxylene production through the use of a split feed reforming process, wherein hydrotreated naphtha is split into light, middle and heavy fractions. Each fraction is reformed separately to generate streams containing aromatic compounds. These streams can further be processed and can undergo dealkylation, transalkylation, disproportionation, isomerization, and separation steps to maximize paraxylene production. In addition, some streams are recycled or recombined in order to maximize paraxylene production.

20 Claims, 4 Drawing Sheets

(56) References Cited

U.S. PATENT DOCUMENTS

| | | | |
|---|---|---|---|
| 2012/0277501 A1* | 11/2012 | Gajda | C10G 59/00 |
| | | | 585/301 |
| 2013/0165719 A1 | 6/2013 | Negiz et al. | |
| 2014/0187832 A1* | 7/2014 | Serban | C10G 59/02 |
| | | | 585/303 |
| 2015/0368571 A1 | 12/2015 | Mehlberg et al. | |
| 2016/0346711 A1 | 12/2016 | Whitchurch | |
| 2018/0186710 A1 | 7/2018 | Abudawoud et al. | |
| 2018/0339954 A1 | 11/2018 | Xu et al. | |

* cited by examiner

PARAXYLENE PRODUCTION FROM NAPHTHA FEED

TECHNICAL FIELD

This document relates to processing hydrocarbon mixtures, for example, hydrocarbons recovered from subsurface reservoirs, into their characteristic components or modified compounds.

BACKGROUND

Hydrocarbons can be retrieved from subsurface reservoirs and are typically refined to produce useful fuels and aromatic compounds. Naphtha, a product of crude oil refining, contains a mixture of different hydrocarbons, including petrochemical building blocks such as benzene and paraxylene. These aromatic compounds have a number of industrial uses, and efficiently isolating paraxylene and other aromatic compounds from naphtha feeds is an important industrial endeavor.

SUMMARY

This disclosure describes a method of producing paraxylene from a hydrotreated naphtha feed.

The following units of measure have been mentioned in this disclosure:

| Unit of Measure | Full form |
| --- | --- |
| °C. | degrees Celsius |
| hr | hour |

Certain aspects of the subject matter described in this disclosure can be implemented as a method. A hydrotreated naphtha feed is split into a light fraction, a middle fraction and a heavy fraction. The light fraction is processed with a first reformer to yield a light reformate. The middle fraction is processed with a second reformer to yield a middle reformate. The heavy fraction is processed with a third reformer to yield a heavy reformate. The heavy reformate is processed with a dealkylation unit to yield a dealkylated heavy aromatics stream. The dealkylated heavy aromatics stream is combined with the light reformate to yield a first mixed heavy aromatics stream. The first mixed heavy aromatics stream is processed with a transalkylation unit to yield a translkylation effluent stream.

An aspect combinable with any of the other aspects can include the following features. The first mixed heavy aromatics stream is processed with a toluene disproportionation functionality reactor.

An aspect combinable with any of the other aspects can include the following features. The heavy reformate is combined with a heavy aromatics stream to form a second mixed heavy aromatics stream, and the second mixed heavy aromatics stream is processed with the dealkylation unit to yield the dealkylated heavy aromatics stream.

An aspect combinable with any of the other aspects can include the following features. The heavy aromatics stream is obtained from a fractionation column.

An aspect combinable with any of the other aspects can include the following features. Processing the second mixed heavy aromatics stream with the transalkylation unit includes processing with a toluene disproportionation functionality reactor.

An aspect combinable with any of the other aspects can include the following features. The middle reformate is processed with a PX separator to yield a PX product stream, a PX separator effluent stream, or both.

An aspect combinable with any of the other aspects can include the following features. The PX separator effluent stream is processed with a xylene isomerization unit to yield a xylene isomerization effluent stream.

An aspect combinable with any of the other aspects can include the following features. The xylene isomerization effluent stream is processed with the fractionation column to yield a xylene product stream.

An aspect combinable with any of the other aspects can include the following features. The middle reformate is combined with the xylene product stream to form a mixed xylene stream. The mixed xylene stream is processed with the PX separator to yield the PX product stream, PX effluent stream, or both.

An aspect combinable with any of the other aspects can include the following features. Processing the PX separator effluent stream with the xylene isomerization unit includes processing with a selective isomerization catalyst.

An aspect combinable with any of the other aspects can include the following features. The xylene product stream is obtained from the fractionation column.

An aspect combinable with any of the other aspects can include the following features. The transalkylation unit effluent stream is processed with the fractionation column to yield an $H_2$ and light gases stream, a benzene product stream, a toluene product stream, the xylene product stream, a heavy aromatics stream, a heavy aromatics bleed, or a combination thereof.

An aspect combinable with any of the other aspects can include the following features. A hydrotreated naphtha feed is split into a light fraction, a middle fraction, and a heavy fraction based on corresponding boiling points in a fractionation column. The light fraction is processed with a first reformer to yield a light reformate. The middle fraction is processed with a second reformer to yield a middle reformate. The heavy fraction is processed with a third reformer to yield a third reformate. Each of the reformers can have a different reformer reactor severity. The heavy reformate is processed with a dealkylation unit to yield a dealkylation effluent stream. The dealkylation effluent stream is combined with the light reformatted and the combined dealkylation effluent stream and light reformate are processed with a transalkylation unit to yield a mixed xylene stream.

An aspect combinable with any of the other aspects can include the following features. The mixed xylene stream is combined with the middle reformate. The combination of the mixed xylene stream and the middle reformate is processed with a PX separator unit to yield a paraxylene separation effluent stream. The paraxylene separation effluent stream is processed with a xylene isomerization unit.

An aspect combinable with any of the other aspects can include the following features. A hydrotreated naphtha feed is split into a light fraction, a middle fraction, and a heavy fraction. The light fraction is processed with a first reformer to yield a light reformate. The middle fraction is processed with a second reformer to yield a middle reformate. The heavy fraction is processed with a third reformer to yield a heavy reformate. The heavy reformate is processed with a dealkylation unit to yield a dealkylated heavy aromatics stream. The middle reformate is processed with a PX separator unit to yield a PX product stream, a PX separator effluent stream, or both. The PX separator effluent stream is processed with a xylene isomerization unit to yield a xylene isomerization unit effluent stream. The xylene isomerization effluent stream, the dealkylation unit effluent stream, and a transalkylation unit effluent stream are processed by a fractionation column to yield an $H_2$ and light gases stream, a benzene product stream, a toluene product stream, the xylene product stream, a bottom stream, or a combination thereof. The bottom stream includes a first heavy aromatics stream and a heavy aromatics bleed. The benzene stream, the toluene stream, the heavy aromatics bleed, the light reformate and a hydrogen stream are combined and the combined streams are processed with a transalkylation unit to yield the transalkylation effluent stream.

An aspect combinable with any of the other aspects can include the following features. The heavy reformate is combined with the first heavy aromatics stream to form a mixed heavy aromatics stream. The mixed heavy aromatics stream is processed with the dealkylation unit to yield the dealkylation effluent stream.

An aspect combinable with any of the other aspects can include the following features. The middle reformate is combined with the xylene product stream to form a mixed xylenes stream. The mixed xylenes stream is process with the PX separator unit to yield the PX product stream, the PX separator effluent stream, or both.

An aspect combinable with any of the other aspects can include the following features. Processing the mixed xylenes stream with the transalkylation unit includes processing with a toluene disproportionation functionality reactor.

An aspect combinable with any of the other aspects can include the following features. Processing with the transalkylation unit includes processing with a selective TMB transalkylation catalyst.

An aspect combinable with any of the other aspects can include the following features. Processing the PX separator effluent stream with the xylene isomerization unit includes processing with a selective isomerization catalyst.

The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Heavy aromatics can be produced from naphtha using a reforming process. A reforming process converts the hydrotreated naphtha feed into aromatics-rich reformate. In a typical aromatics complex, a reformate stream is sent to a benzene, toluene and xylene (BTX) splitter, which separates the components of the reformate stream into benzene, toluene, and xylene streams. The xylene stream is subsequently sent to a xylene splitter, where aromatics with 10 or more carbons are rejected, aromatics with 9 carbons are sent to transalkylation steps to create more BTX, and extracted xylenes are sent to a paraxylene separation step. This paraxylene separation step yields paraxylene as well as mixed xylenes. The mixed xylenes can then undergo a stand alone isomerization step to form additional paraxylene. Toluene produced by the BTX splitter can undergo disproportionation to yield benzene and mixed xylenes.

Provided in this disclosure, in part, are methods for reforming naphtha. These methods allow for maximizing paraxylene production. In some implementations, a hydrotreated naphtha feed is split into three fractions of light, middle, and heavy hydrocarbons. These three fractions are processed separately to yield light, middle and heavy reformates. Combinations of the reformates then undergo reactions that maximize paraxylene production, such as dealkylation, transalkylation, isomerization, separation reactions, or a combination thereof. One advantage of splitting the naphtha feed before reforming the naphtha feed is an increase in the amount of aromatic compounds recovered as well as an increase in the amount of paraxylene recovered. Another advantage of this process is that the heavy aromatic compounds are not rejected, but utilized to increase the amount of paraxylene recovered.

The use of a split-feed reformer process improves the aromatics yields in terms of weight percentage of the total feed compared to a traditional whole-feed naphtha reforming process. This can be seen in chemical process simulations, for example Aspen HYSYS process simulations. Two HYSYS simulations were carried out at the same reactor weighted average inlet temperature (WAIT) of 522.7° C. (Table 1). The reformate (with materials with more than 5 carbons) from the split feed reformer has a research octane number (RON) of 104.2, whereas the reformate from the whole feed reformer at the same WAIT has a RON of 102.5. Table 1 shows the total aromatics yield increases from 71.5 wt % to 73.3 wt %.

TABLE 1

Comparison of Whole Naphtha Feed vs. Split Naphtha Feed Process Simulations

|  | Whole Naphtha Feed | Split Naphtha Feed | Delta |
| --- | --- | --- | --- |
| Benzene, wt % | 2.1 | 2.4 | 0.3 |
| Toluene, wt % | 11.9 | 12.8 | 0.9 |
| Ethyl Benzene, wt % | 5.0 | 5.0 | 0 |
| Mixed Xylene, wt % | 25.1 | 25.1 | 0 |
| Aromatics (9 carbons), wt % | 23.4 | 24.1 | 0.7 |
| Aromatics (10 carbons), wt % | 3.5 | 3.6 | 0.1 |
| Aromatics (11+ carbons), wt % | 0.4 | 0.4 | 0 |
| Total Aromatics, wt % | 71.5 | 73.3 | 1.8 |

Figure 1:
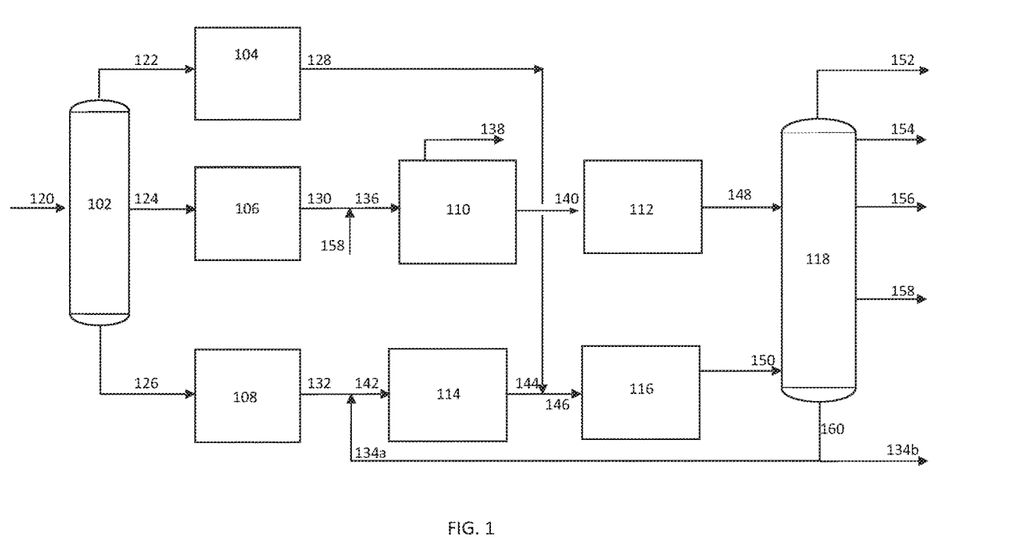
FIG. 1 shows an example of a processing system for reforming naphtha.
Figure 2:
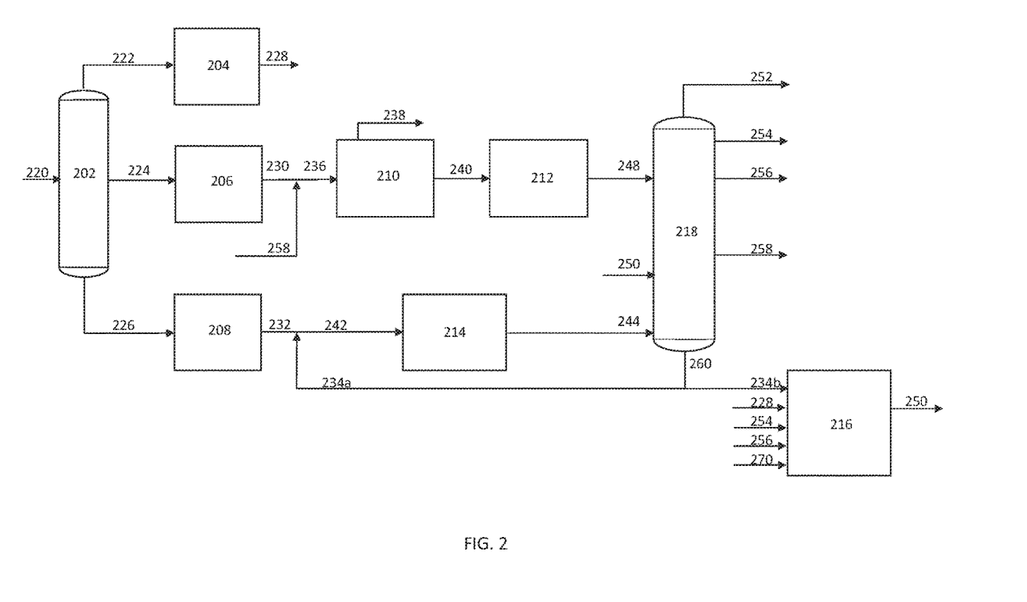
FIG. 2 shows an example of a processing system for reforming naphtha.

FIGS. 1 and 2 describe a processing system for processing a naphtha feed. Components of the system are described in the paragraphs that follow with reference to FIGS. 1 and 2.

Naphtha Splitter (102, 202)

A naphtha splitter (102, 202) is used to split a hydrotreated naphtha feed. The naphtha splitter can include a distillation column that splits the hydrotreated naphtha feed into fractions based on boiling point, with the end cut point for light fractions between 100° C. and 120° C. and the end cut point for middle fractions between 130° C. and 150° C., for example with end cut point for light fractions at around 110° C. and end cut point for middle fractions at around 140° C. The end cut points can also be adjusted to modify the flowrate.

Processing with the naphtha splitter results in three fractions: a light fraction (122, 222), a middle fraction (124, 224), and a heavy fraction (126, 226). The light fraction (122, 222) contains compounds with 6-7 carbons, the middle fraction (124, 224,) contains compounds with 8 carbons, and the heavy fraction (126, 226) contains compounds with 9 or more carbons.

Reformers (104, 106, 108, 204, 206, 208)

A reformer can be used on each of the split feed fractions. In general, the reformers convert paraffinic and naphthenic materials into aromatics and hydrogen. Each naphtha feed fraction can be processed with a dedicated reformer, and each reformer can have a different reactor severity, in order to produce higher aromatic content in the reformate while minimizing light gas production, for example by avoiding excess hydrocracking in the reformer reactor.

In some implementations, a first reformer (104, 204) can be used to reform the light fraction (122, 222), which yields the light reformate (128, 228). The light reformate contains aromatic compounds with 6-7 carbons.

A second reformer (106, 206) can be used to reform the middle fraction (124, 224), which yields the middle reformate (130, 230). The middle reformate contains aromatic compounds with 8 carbons.

A third reformer (108, 208), can be used to reform the heavy fraction (126, 226), which yields the heavy reformate. The heavy reformate contains aromatic compounds with 9 or more carbons.

Paraxylene (PX) Separator (110, 210)

In some implementations, reformate streams, combined streams, or effluent streams can be processed using a PX separator (110, 210), using separation techniques such as distillation or crystallization. The PX separator can be used to process the middle reformate (130, 230), or a mixed xylene stream (136, 236). The mixed xylene stream is a combination of the middle reformate (130, 230) and a xylene product stream (158, 258). Processing either the middle reformate (130, 230) or the mixed xylene stream (136, 236) yields at least one of a PX product stream (138, 238) which includes paraxylene and a PX separator effluent stream (140, 240) which includes orthoxylene, metaxylene, and ethylbenzene.

Xylene Isomerization Unit (112, 212)

Reformate streams, combined streams, or effluent streams which contain orthoxylene and metaxylene can undergo xylene isomerization using a xylene isomerization unit (112, 212). In some implementations, the xylene isomerization unit includes a selective isomerization catalyst, and the streams processed by the standard xylene isomerization unit can undergo isomerization to yield orthoxylene, metaxylene, and paraxylene in thermal equilibrium. The xylene isomerization unit (112, 212) can be used to process the PX separator effluent stream (140, 240), which yields the xylene isomerization unit effluent (148, 248). The xylene isomerization unit effluent (148, 248) includes orthoxylene, metaxylene, and paraxylene in thermal equilibrium.

Dealkylation Unit (114, 214)

In some implementations, reformate streams, combined streams, or effluent streams undergo selective dealkylation using a dealkylation unit (114, 214). The selective dealkylation process includes removing alkyl chains with two or more carbons from an aromatic base under the presence of hydrogen, while minimizing demethylation. The main products of the dealkylation process include benzene, toluene, xylenes, and trimethylbenzene. The dealkylation reaction can include a dealkylation catalyst. The dealkylation unit (114, 214) can be used to process the heavy reformate (132, 232) or a second mixed heavy aromatics stream (142, 242). The second mixed heavy aromatics stream (142, 242) is a combination of the heavy reformate (132, 232) and a heavy aromatics stream (134a, 234a). Processing either the heavy reformate (132, 232) or the second mixed heavy aromatics stream (142, 242) yields a dealkylated heavy aromatics stream (144, 244), which includes benzene, toluene, xylenes, trimethylbenzene, methylethylbenzene (C9), and C10+ aromatics.

Transalkylation Unit (116, 216)

Reformate streams, combined streams, or effluent streams can undergo transalkylation with a transalkylation unit (116, 216). The major transalkylation reaction is the reaction of C7 compounds with C9 compounds to yield C8 compounds, for example the reaction of toluene with trimethylbenzene to yield xylenes. The minor transalkylation reaction is the reaction of two C9 compounds to form a C8 compound and a C10 compound, for example, the reaction of two trimethylbenzenes to yield xylene and a C10 compound. The transalkylation unit (116, 216) can operate in a temperature range of 200-540° C., with a pressure range of 10-50 bar, a liquid hourly space velocity range of 1-20/hr, and a hydrogen to feed ratio range of 0-8. The transalkylation unit can include a catalyst, and the catalyst can be any selective trimethylbenzene (TMB) transalkylation catalyst. In addition, the transalkyation unit can include toluene disproportionation functionality, where two C7 compounds can react to yield a C8 and a C6 compound. For example, two toluenes can react to form xylenes and benzene.

In some implementations, the transalkylation unit (116) can be used to process the dealkylated heavy aromatics stream (144) or a first mixed heavy aromatics stream (146). The first mixed heavy aromatics stream is a combination of the dealkylated heavy aromatics stream (144) and the light reformate (128). Processing the dealkylated heavy aromatics stream (144) or the first mixed heavy aromatics stream (146) yields the transalkylation unit effluent (150), which includes xylenes and unreacted toluene, C9, and C10+ aromatics.

In some implementations, the transalkylation unit (216) can be used to process the combination of a heavy aromatics bleed (234b), the light reformate (228), a benzene product stream (254), a toluene product stream (256), and a hydrogen stream (270) to yield the transalkylation unit effluent (250), which includes xylenes (and unreacted toluene, C9, and C10+ aromatics.

Fractionation Column (118, 218)

A fractionation column (118, 218) can be used to separate streams or effluents by boiling point into specific components. For example, the xylene isomerization unit effluent (148, 248), the transalkylation unit effluent (150, 250), and the dealkylated heavy aromatics stream (244), can all be processed with a fractionation column. Fractionation can yield one or more product streams, for example an $H_2$ and light gasses stream (152, 252), a benzene product stream (154, 254), a toluene product stream (156, 256), a xylene product stream (158, 258), and a bottom stream (160, 260). The bottom stream (160, 260) includes mainly C9 aromatics and some C10+ aromatics. The bottom stream can be further split into the heavy aromatics stream (134a, 234a) and the heavy aromatics bleed (134b, 234b), a physical splitting that removes part of the stream as a bleed and allows the remaining product stream to be recycled for optimum production. Some or all of these product streams can be recombined with other streams to undergo further processing.

In addition, the naphtha processing system can include a flow control system to flow the streams between units and/or columns. In some implementations, the flow control systems can include one or more pumps, one or more flowlines, one or more valves, or any combination of them. The flow control system can additionally include a flow controller, for example, a computer-readable medium storing instructions executable by one or more computer processors to perform operations including controlling the flow of the different streams between the different units of the naphtha processing system. In some implementations, the flow controller can automatically, that is, without user intervention, control the one or more pumps or the one or more valves or other components of the flow control system based, in part, on process conditions in the naphtha processing system. In some implementations, the flow controller can perform these operations in response to receiving instructions from an operator, for example, via a user interface displayed on a display device of a computer system connected to the flow controller.

Example 1

Figure 3:
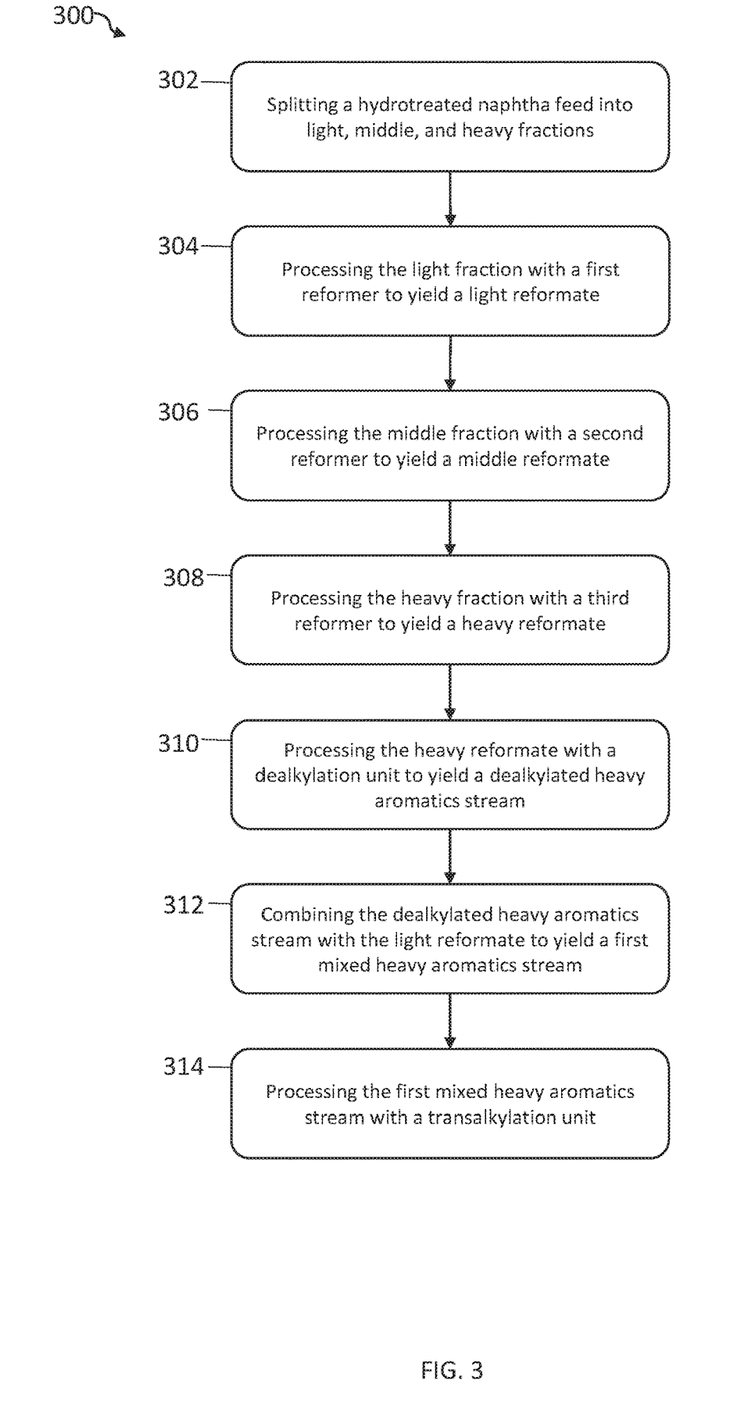
FIG. 3 is a flow chart showing an example of a method of processing a hydrotreated naphtha feed using the processing system of FIG. 1.

FIG. 3 is a flow chart showing an example of a method of processing a hydrotreated naphtha feed using the processing system shown in FIG. 1. At 302, a hydrotreated naphtha feed is split into light, middle, and heavy fractions. For example, FIG. 1 shows an example of a processing system for reforming naphtha where a hydrotreated naphtha feed (120) is processed with a naphtha splitter (102), which splits the naphtha into light (122), middle (124) and heavy (126) fractions. Each of these streams can then be reformed separately, with a dedicated reformer (104, 106, 108).

At 304, the light fraction (122) is reformed with a first reformer (104) to yield a light reformate stream (128). At 306, the middle fraction (124) is reformed with a second reformer (106) to yield a middle reformate stream (130). At 308, the heavy fraction (126) is reformed with a third reformer (108) to yield a heavy reformate stream (132).

At 310, the heavy reformate (132) can be further processed with a dealkylation unit (114) to yield a dealkylated heavy aromatics stream (144). The dealkylated heavy aromatics stream can then be combined at 312 with the light reformate (128) to generate a first mixed heavy aromatics stream (146). The first mixed heavy aromatics stream (146) can then be processed at 314 with a transalkylation unit (116) to yield a transalkylation effluent stream (150).

The transalkylation effluent stream (150) can be further processed by fractionation, for example with a fractionation column (118), resulting in one or more of the product streams (152, 154, 156, 158 and 160).

In some implementations, the heavy reformate (132) can be combined with the heavy aromatics stream (134a) from the fractionation column (118) to form a second mixed heavy aromatics stream (142). The second mixed heavy aromatics stream (142) can be processed with the dealkylation unit (114) to yield the dealkylated heavy aromatics stream (144).

The middle reformate (130) can be processed with a PX separator (110) to yield at least one of a PX product stream (138) and a PX effluent stream (140). The PX effluent stream (140) can be further processed with a xylene isomerization unit (112) to yield a xylene isomerization unit effluent stream (148). The xylene isomerization effluent stream (148) can be further processed by fractionation, for example by a fractionation column (118), which yields mainly the xylene product stream (158).

In some implementations, the middle reformate can be combined with the xylene product stream (158) from the fractionation column (118) to create a mixed xylene stream (136). The mixed xylene stream can be processed with the PX separator to yield at least one of the PX product stream (138) or the PX effluent stream (140).

Example 2

Figure 4:
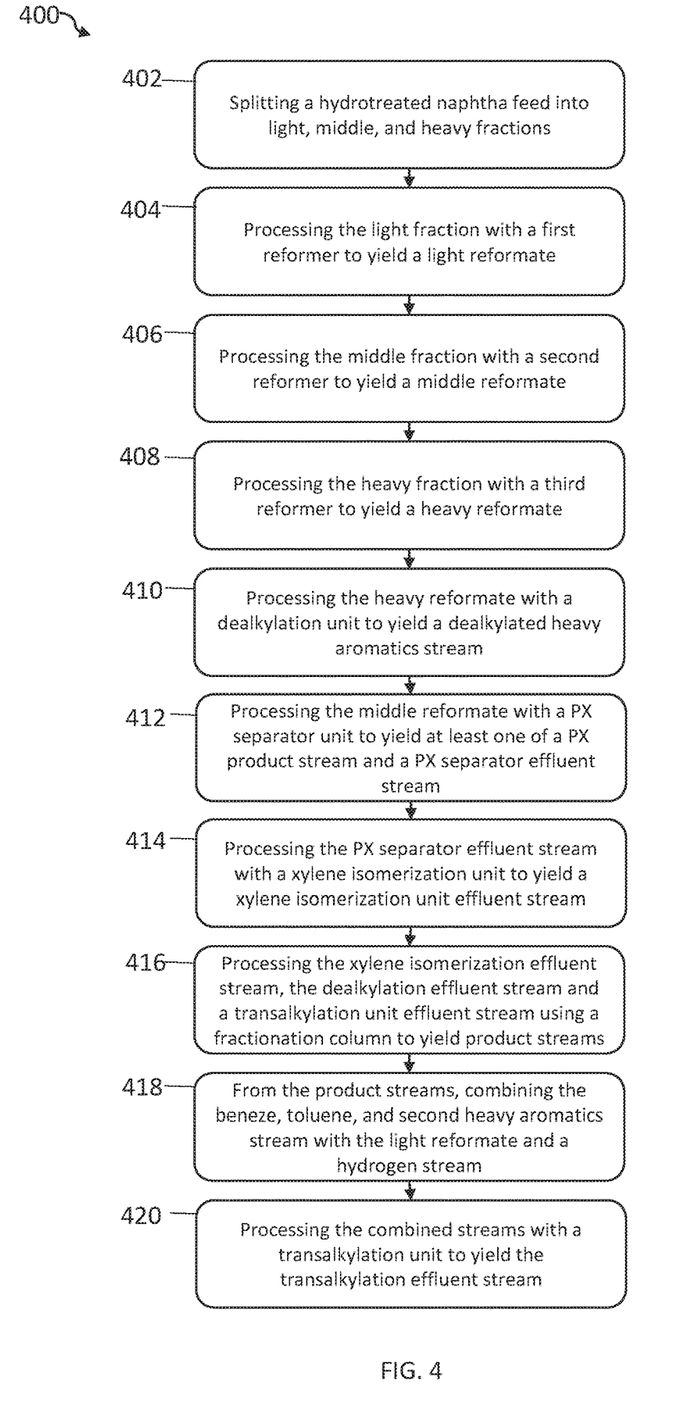
FIG. 4 is a flow chart showing an example of a method of processing a hydrotreated naphtha feed using the processing system of FIG. 2.

FIG. 4 is a flow chart showing an example of a method of processing a hydrotreated naphtha feed. At 402, a hydrotreated naphtha feed is split into light, middle, and heavy fractions. For example, FIG. 2 shows an example of a processing system for reforming naphtha where a hydrotreated naphtha feed (220) is processed with a naphtha splitter (202), which splits the naphtha into a light fraction (222), a middle fraction (224), and a heavy fraction (226). At 404, the light fraction can be processed with a first reformer (204) to yield a light reformate (228). At 406, the middle fraction can be processed with a second reformer (206) to yield a middle reformate (230). At 408, the heavy fraction can be processed with a third reformer (208) to yield a heavy reformate (232). At 410, the heavy reformate can be further processed with a dealkylation unit (214) to yield a dealkylated heavy aromatics stream (244). At 412, the middle reformate can be processed with a PX separator unit (210) to yield at least one of a PX product stream (238) and a PX separator effluent stream (240). At 414, the PX separator effluent stream can be further processed with a xylene isomerization unit (212) to yield a xylene isomerization unit effluent stream (248).

At 416, the xylene isomerization effluent stream (248), the dealkylation effluent stream (244), and a transalkylation unit effluent stream (250) can be processed using a fractionation column (218). Processing the xylene isomerization effluent stream yields the xylene product stream (258). Processing the dealkylation effluent stream (244) yields at least one of the product streams (252, 254, 256, 258, 260). Processing the transalkylation unit effluent (250) yields at least one of the product streams (252, 254, 256, 258, 260). The bottom stream (260) can be split into a first heavy aromatics stream (234a) and the heavy aromatics bleed (234b).

At 418, the benzene stream (254), the toluene stream (256), the heavy aromatics bleed (234b), the light reformate stream (228) and a hydrogen stream (270) are combined and further processed at 420 with a translkylation unit (216) to yield the transalkylation effluent stream (250).

In some implementations, the heavy reformate (232) can be combined with the heavy aromatics stream (234a) recovered from the fractionation column (118) to create a first mixed heavy aromatics stream (242). The mixed heavy aromatics stream (242) can be processed with a dealkylation unit to yield the dealkylated heavy aromatics stream (244).

In some implementations, the middle reformate (230) is combined with the xylene product stream (258) recovered from the fractionation column (118) to form a mixed xylenes stream (236). The mixed xylenes stream (236) can be processed with the PX separator unit to yield at least one of the PX product stream (238) and the PX separator effluent stream (240).

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

The term "room temperature" as used in this disclosure refers to a temperature of about 15 degrees Celsius (° C.) to about 28° C.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

In the paragraphs above, reference has been made in detail to certain embodiments of the disclosed subject matter, examples of which are illustrated in part in the accompanying drawings. While the disclosed subject matter has been described in conjunction with the enumerated claims, it will be understood that the exemplified subject matter is not intended to limit the claims to the disclosed subject matter.

As used in this disclosure, the terms "C6," "C7," "C8," "C9," "C10," and "C10+" refer to compounds with 6, 7, 8, 9, 10, or 10 or more carbon atoms, respectively.

A number of implementations of the disclosure have been described. Nevertheless, it will be understood that various modifications may be made without departing from the spirit and scope of the disclosure.

What is claimed is:

1. A method comprising:
splitting a hydrotreated naphtha feed into a light fraction, a middle fraction, and a heavy fraction;
processing the light fraction with a first reformer to yield a light reformate;
processing the middle fraction with a second reformer to yield a middle reformate;
processing the heavy fraction with a third reformer to yield a heavy reformate;
processing the heavy reformate with a dealkylation unit to yield a dealkylated heavy aromatics stream;
combining the dealkylated heavy aromatics stream with the light reformate to yield a first mixed heavy aromatics stream; and
processing the first mixed heavy aromatics stream with a transalkylation unit to yield a transalkylation effluent stream.

2. The method of claim 1, wherein processing the first mixed heavy aromatics stream with the transalkylation unit comprises processing with a toluene disproportionation functionality reactor.

3. The method of claim 1, further comprising:
combining the heavy reformate with a heavy aromatics stream to form a second mixed heavy aromatics stream: and
processing the second mixed heavy aromatics stream with the dealkylation unit to yield the dealkylated heavy aromatics stream.

4. The method of claim 3, wherein the heavy aromatics stream is obtained from a fractionation column.

5. The method of claim 3, further comprising processing the second mixed heavy aromatics stream with the transalkylation unit comprises processing with a toluene disproportionation functionality reactor.

6. The method of claim 1, further comprising processing the middle reformate with a PX separator to yield at least one of a PX product stream or a PX separator effluent stream.

7. The method of claim 6, further comprising processing the PX separator effluent stream with a xylene isomerization unit to yield a xylene isomerization effluent stream.

8. The method of claim 7, further comprising processing the xylene isomerization effluent stream with a fractionation column to yield a xylene product stream.

9. The method of claim 8, further comprising combining the middle reformate with the xylene product stream to form a mixed xylene stream and processing the mixed xylene stream with the PX separator to yield at least one of the PX product stream or the PX separator effluent stream.

10. The method of claim 7, wherein processing the PX separator effluent stream with the xylene isomerization unit comprises processing with a selective isomerization catalyst.

11. The method of claim 9, wherein the xylene product stream is obtained from the fractionation column.

12. The method of claim 1, further comprising processing the transakylation unit effluent stream with the fractionation column to yield at least one of:
an H$_2$ and light gases stream;
a benzene product stream;
a toluene product stream;
the xylene product stream;
a heavy aromatics stream; and
the heavy aromatics bleed.

13. A method comprising:
splitting a hydrotreated naphtha feed into a light fraction, a medium fraction and a heavy fraction, each based on a corresponding boiling point in a distillation column;
processing the light fraction, the middle fraction and the heavy fraction with a first reformer, a second reformer and a third reformer, respectively, to yield a light reformate, a medium reformate and a heavy reformate, respectively, wherein the first reformer, the second reformer and the third reformer have differing reformer reactor severities;
processing the heavy reformate with a dealkylation unit to yield a dealkylation effluent stream;
combining the dealkylation effluent stream with the light reformate; and
processing the combined dealkylation effluent stream and the light reformate with a transalkylation unit to yield a mixed xylene stream.

14. The method of claim 13, further comprising:
combining the mixed xylene stream with a middle reformate;
processing the combined mixed xylene stream and the middle reformate with a PX separator to yield a PX separator effluent stream; and
processing the PX separator effluent stream with a xylene isomerization unit.

15. A method comprising:
splitting a hydrotreated naphtha feed into a light fraction, a middle fraction, and a heavy fraction;
processing the light fraction, the middle fraction and the heavy fraction with a first reformer, a second reformer and a third reformer, respectively, to yield a light reformate, a middle reformate and a heavy reformate, respectively;
processing the heavy reformate with a dealkylation unit to yield a dealkylated heavy aromatics stream;
processing the middle reformate with a PX separator unit to yield at least one of a PX product stream and a PX separator effluent stream;
processing the PX separator effluent stream with a xylene isomerization unit to yield a xylene isomerization unit effluent stream;

processing the xylene isomerization effluent stream, a dealkylation effluent stream, and a transalkylation unit effluent stream using a fractionation column to yield:
- an $H_2$ and light gases stream,
- a benzene product stream,
- a toluene product stream,
- a xylene product stream,
- a bottom stream, the bottom stream further comprising
  - a first heavy aromatics stream, and
  - a heavy aromatics bleed, and combining the benzene product stream, the toluene product stream, the heavy aromatics bleed, the light reformate stream and a hydrogen stream; and processing the combined streams with a transalkylation unit to yield the transalkylation effluent stream.

16. The method of claim 15, further comprising combining the heavy reformate with the first heavy aromatics stream to form a mixed heavy aromatics stream before processing the mixed heavy aromatics stream with the dealkylation unit to yield the dealkylation effluent stream.

17. The method of claim 15, further comprising combining the middle reformate with the xylene product stream to form a mixed xylenes stream before processing the mixed xylenes stream with the PX separator unit to yield at least one of the PX product stream, or the PX separator effluent stream.

18. The method of claim 15, wherein processing the combined streams with the transalkylation unit comprises processing with a toluene disproportionation functionality reactor.

19. The method of claim 15, wherein processing the combined streams with the transalkylation unit comprises processing with a selective TMB transalkylation catalyst.

20. The method of claim 15, wherein processing PX separator effluent stream with the xylene isomerization unit comprises processing with a selective isomerization catalyst.

* * * * *

UNITED STATES PATENT AND TRADEMARK OFFICE
CERTIFICATE OF CORRECTION

PATENT NO. : 10,941,356 B2  
APPLICATION NO. : 16/454839  
DATED : March 9, 2021  
INVENTOR(S) : He et al.

Page 1 of 1

It is certified that error appears in the above-identified patent and that said Letters Patent is hereby corrected as shown below:

In the Claims

Column 10, Line 18, Claim 12, delete "transakylation" and insert -- transalkylation --.

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*